(12) United States Patent
Mydlack et al.

(10) Patent No.: US 7,170,592 B2
(45) Date of Patent: Jan. 30, 2007

(54) METHOD OF INSPECTING A SPHERE WITHOUT ORIENTING THE SPHERE

(75) Inventors: Thomas L Mydlack, Rochester, MA (US); Paul A Furze, Tiverton, RI (US)

(73) Assignee: Acushnet Company, Fairhaven, MA (US)

( * ) Notice: Subject to any disclaimer, the term of this patent is extended or adjusted under 35 U.S.C. 154(b) by 185 days.

(21) Appl. No.: 10/797,798

(22) Filed: Mar. 10, 2004

(65) Prior Publication Data

US 2005/0200837 A1 Sep. 15, 2005

(51) Int. Cl.
G01N 21/88 (2006.01)
G06K 9/00 (2006.01)

(52) U.S. Cl. .................. 356/237.1; 356/394; 382/154

(58) Field of Classification Search .. 356/237.1–237.6, 356/394, 601, 606–608, 429, 431; 250/223 R, 250/330; 382/149, 154, 289, 110
See application file for complete search history.

(56) References Cited

U.S. PATENT DOCUMENTS

| | | | | |
|---|---|---|---|---|
| 4,240,620 A | | 12/1980 | Tunkers | 269/24 |
| 4,246,606 A | * | 1/1981 | Yoshida | 348/129 |
| 4,445,628 A | | 5/1984 | Cain | 222/66 |
| 4,555,635 A | * | 11/1985 | Yoshida | 250/559.46 |
| 5,223,679 A | | 6/1993 | Yoo | 187/134 |
| 5,467,192 A | * | 11/1995 | Manning | 356/613 |
| 5,604,550 A | | 2/1997 | White | 396/429 |
| 5,611,723 A | | 3/1997 | Mitoma et al. | 451/6 |
| 5,703,687 A | | 12/1997 | Kumagai et al. | 356/426 |
| 5,777,244 A | | 7/1998 | Kumagai et al. | 73/865.8 |
| 5,903,341 A | | 5/1999 | Perry et al. | 356/237 |
| 5,966,213 A | * | 10/1999 | Shimosaka et al. | 356/613 |
| 6,031,933 A | | 2/2000 | Kumagai | 382/141 |
| 6,061,126 A | * | 5/2000 | Yoshimura et al. | 356/237.1 |
| 6,262,803 B1 | * | 7/2001 | Hallerman et al. | 356/603 |
| 6,450,082 B1 | | 9/2002 | Sawdon | 92/23 |
| 6,462,303 B1 | | 10/2002 | Brown | 219/121.69 |
| 6,462,812 B1 | | 10/2002 | Heene et al. | 356/237.1 |
| 6,594,623 B1 | * | 7/2003 | Wang et al. | 703/1 |
| 6,608,687 B1 | | 8/2003 | Rulevich et al. | 356/601 |
| 6,630,998 B1 | | 10/2003 | Welchman et al. | 356/394 |
| 6,768,509 B1 | * | 7/2004 | Bradski et al. | 348/207.99 |
| 6,798,515 B1 | * | 9/2004 | Bachelder et al. | 356/397 |
| 6,798,925 B1 | * | 9/2004 | Wagman | 382/287 |
| 2002/0135743 A1 | | 9/2002 | Gindele | 355/18 |
| 2003/0095178 A1 | | 5/2003 | Shibayama | 348/46 |

OTHER PUBLICATIONS

"Increasing Step Motor Performance" from Industrial Devices Corp.
Method of Calibrating a Detector and Calibration Sphere for the Same, U.S. Appl. No. 10/776,429.

\* cited by examiner

*Primary Examiner*—Sang H. Nguyen

(57) ABSTRACT

The present invention is directed to a method of inspecting a curved object comprising the steps of acquiring inspection image data of a curved object using a detector, generating adjusted image data by adjusting the inspection image data, and comparing the adjusted image data with digitally generated image data of a predetermined image. In one embodiment, golf balls are inspected using a line scan camera and a line of coplanar and parallel, diffuse light that uniformly illuminates the camera's scan line. A method of digitally filtering brightness in a digital image is also disclosed.

30 Claims, 7 Drawing Sheets

METHOD OF INSPECTING A SPHERE WITHOUT ORIENTING THE SPHERE

FIELD OF THE INVENTION

This invention generally relates to a method of inspecting a curved object without first orienting the object. This invention more particularly relates to a method a inspecting a golf ball with a vision detection system that does not require orienting the golf ball.

BACKGROUND OF THE INVENTION

One process in golf ball production is the inspection of a golf ball's indicia (e.g., labels, logos, or other markings). After a golf ball is marked with such indicia, it is inspected to ensure that they are properly positioned on the golf ball's surface with minimal defect or blemish.

Various systems automate this process by using a camera that captures images of the indicia and a computer that compares the inspected images with one or more reference images of indicia on an exemplary golf ball, i.e., a golf ball that has no indicia defect or blemish.

A problem associated with this approach, however, is curvature distortion in the two-dimensional images of a three-dimensional curved golf ball. Because the indicia wrap around the ball according to its curvature, the further an indicium is from the point on the golf ball closest to the camera, the more distorted it appears. As the indicia are positioned away from the camera, they appear shortened and bunched together. When viewed by an area scan camera, the further an indicium departs from the center of the golf ball in any direction, the greater the curvature distortion. U.S. Pat. No. 6,462,812 discloses a system that uses an area scan camera to automatically inspect golf balls, but only after the system first orients the indicia directly in front of the camera, to account for curvature distortion in the golf ball inspection images.

U.S. Pat. No. 6,630,998 B1 discloses a golf ball inspection system that uses a line scan camera that requires preliminary orientating golf ball indicia directly in front of the camera, to account for curvature distortion. This commonly owned patent is incorporated herein by reference in its entirety. A line scan camera is a camera that captures a row of pixels. As a golf ball rotates, the line scan camera captures multiple such rows of pixels, which are then assembled to form a two-dimensional image of the golf ball's curved surface. This image captures the golf ball's indicia so that it can be automatically compared with a pre-selected reference or master image of an acceptable golf ball. A line scan camera does not eliminate curvature distortion on the scanned image.

To provide a meaningful basis for inspection, the systems disclosed in the '812 and '998 patents capture scanned images under conditions that are similar to the conditions under which the stored master image was obtained. As mentioned above, these systems orient inspected balls so that when scanned, the orientation of the scanned images should, as closely as possible, match orientation of the master image. It typically takes between 1.5 to 2 seconds to orient each ball. In addition, orienting inaccuracy also requires loosening of inspection standards. If a golf ball is not perfectly centered in front of a camera, application of stringent inspection standards could cause an acceptable golf ball to be rejected. Plus, accurately orienting a ball requires the added step of preliminarily detecting an indicium's original position before the golf ball can be oriented.

Hence, there remains a need for inspecting golf balls and other curved objects without orienting.

SUMMARY OF THE INVENTION

Hence, the present invention is directed to a method of inspecting a curved object that does not require orienting the object.

The present invention is also directed to a method of inspecting a curved object that corrects the curvature distortion on the scanned images.

The present invention is also directed to a method of inspecting a curved object that illuminates the object with diffuse and uniform light.

One aspect of the present invention is directed to using multiple digital scan cameras to acquire an image of the entire surface of the ball. The cameras can be area scan camera, line scan camera or both.

Another aspect of the invention involves making a composite image of object from several line scan or area scan images, so that indicia may be inspected even if it is not seen entirely in one scanned image.

Another aspect of the present invention is directed to a method of inspecting a curved object comprising the steps of acquiring an inspection image of a curved object using a detector, adjusting the inspection image to minimize curvature distortion in an adjusted image, and comparing the adjusted image with a predetermined master image. The adjustment for curvature distortion may include the step of adjusting the locations of the pixels in the inspection image to create the adjusted image for comparing to the master image. The object can be a golf ball. The detector can be a line scan camera that scans the object at a scan line that defines a plane, an area scan camera or any device that can produce a digital image.

In accordance with another aspect of the present invention, the scanned image is adjusted for non-uniform illumination. This method may comprise the steps of acquiring a scanned image of a uniformly shaded object, measuring brightness values for each pixel in said scanned image, calculating a reference brightness value, establishing scale factors for each pixel in said scanned image based on the reference brightness value, and adjusting corresponding pixel brightness values in the inspection image by applying the scale factors.

BRIEF DESCRIPTION OF THE DRAWINGS

In the accompanying drawings, which form a part of the specification and are to be read in conjunction therewith and in which like reference numerals are used to indicate like parts in the various views.

DETAILED DESCRIPTION OF THE PREFERRED EMBODIMENTS

As illustrated in the accompanying drawings and discussed in detail below, one aspect of the present invention is directed to a method of inspecting an object having a curved three-dimensional surface. One problem associated with the automated inspection of curved objects is curvature distortion, which is illustrated below. Additionally, while the examples discussed below use a line scan camera, it is noted that line scan cameras are used for illustrative purpose only and the present invention is not limited to line scan cameras.

Figure 1:
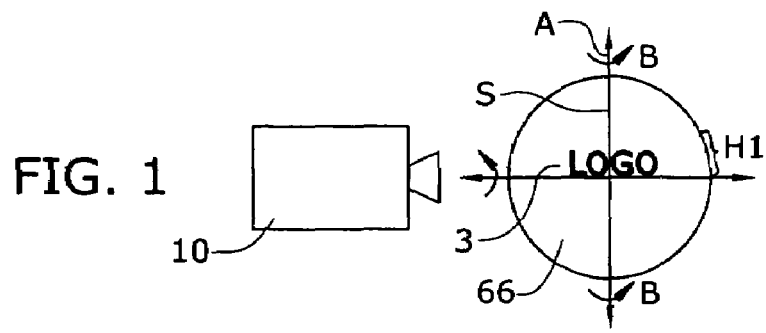
FIG. 1 is a schematic perspective view of a line scan camera and a golf ball with a printed indicium.
Figure 2:
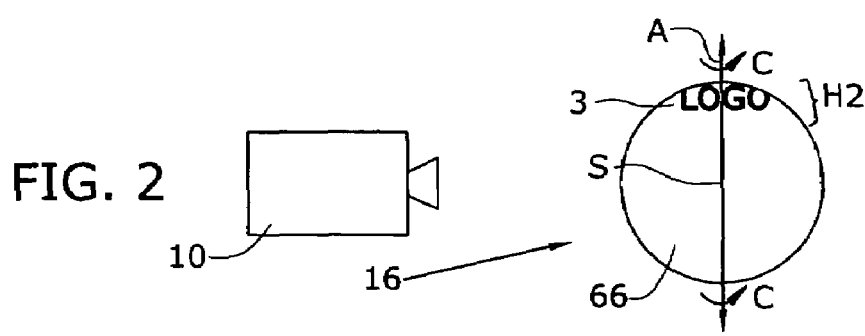
FIG. 2 is a schematic perspective view of the line scan camera and the golf ball of FIG. 1 after the golf ball has been rotated upwards so that its indicium no longer directly faces the camera.

Referring to FIGS. 1 and 2, indicium 3 on ball surface 13 is rotated about 70 degrees from horizontal axis H. Because indicium 3 is shifted to away from the equator, it appears shorter than it does in FIG. 1, i.e., indicium 3's apparent height H2 in FIG. 2 is less than apparent height H1 in FIG. 1, due to curvature distortion.

Figure 3:
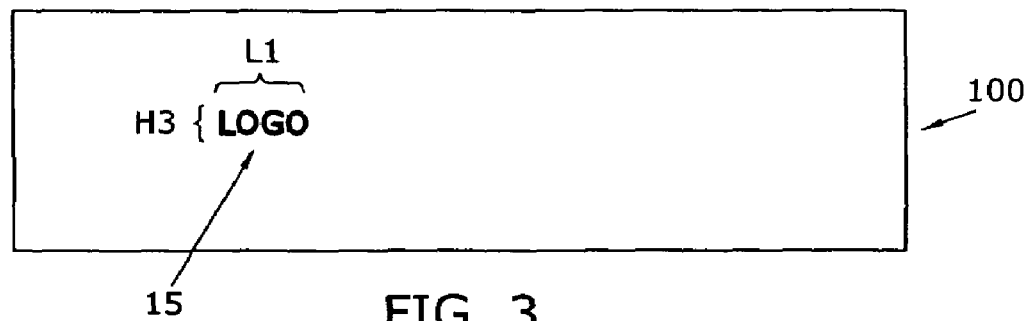
FIG. 3 is a plan view of a scanned image made by the line scan camera of the golf ball in FIG. 1.

In FIG. 1, indicium 3 is located directly in front of camera 10. Line scan camera 10 scans ball 66 at scan line S as ball 66 rotates about vertical axis A in the direction indicated by arrows B. In FIG. 3, when the detected data is assembled, scanned image 100 includes indicium 3 as logo image portion 15. Logo image portion 15 captures indicium 3 as it appears on ball 66 when indicium 3 is viewed head on by the camera. Image portion 15's relative length L1 and height H3 are substantially the same as the true dimensions of indicium 3.

Figure 4:
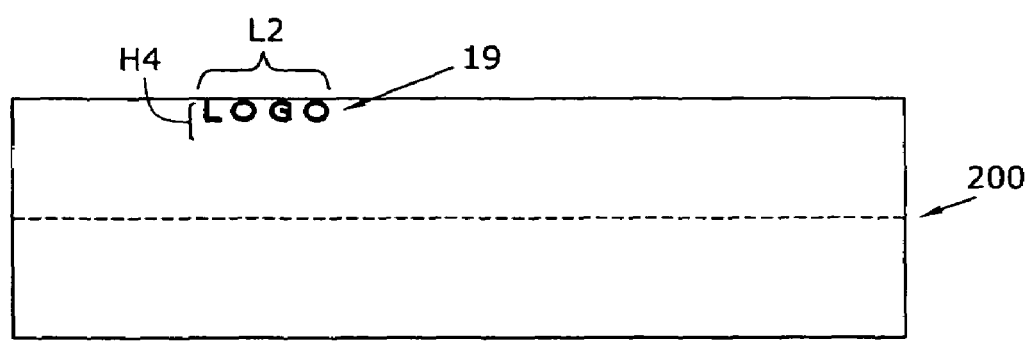
FIG. 4 is a plan view of a scanned image made by the line scan camera of the golf ball in FIG. 2.

In FIG. 2, indicium 3 is located away from the equator of rotating ball 66. Again, line scan camera 10 scans ball 66 at scan line S as ball 66 rotates about vertical axis A in the direction indicated by arrows C. Referring to FIG. 4, when the detected data is assembled, scanned image 200 depicts indicium 3 as logo image portion 19. Logo image portion 19 depicts indicium 3 as being both shorter in height and longer in length than its actual appearance on ball 66. Thus, logo image 19 contains curvature distortion.

Accordingly, one aspect of the present invention is directed to a method of inspecting a curved object that minimizes curvature distortion without orientating the curved object. First, an inspection image is scanned or otherwise acquired. Then, the data that makes up the image is adjusted so that an adjusted image with minimal curvature distortion is obtained. Finally, the adjusted image is compared with a master image that is preferably digitally generated. In one embodiment, the adjusted image is automatically compared with the master image by an analyzer that compares the data from the adjusted image with the data from the digitally generated image.

Figure 5:
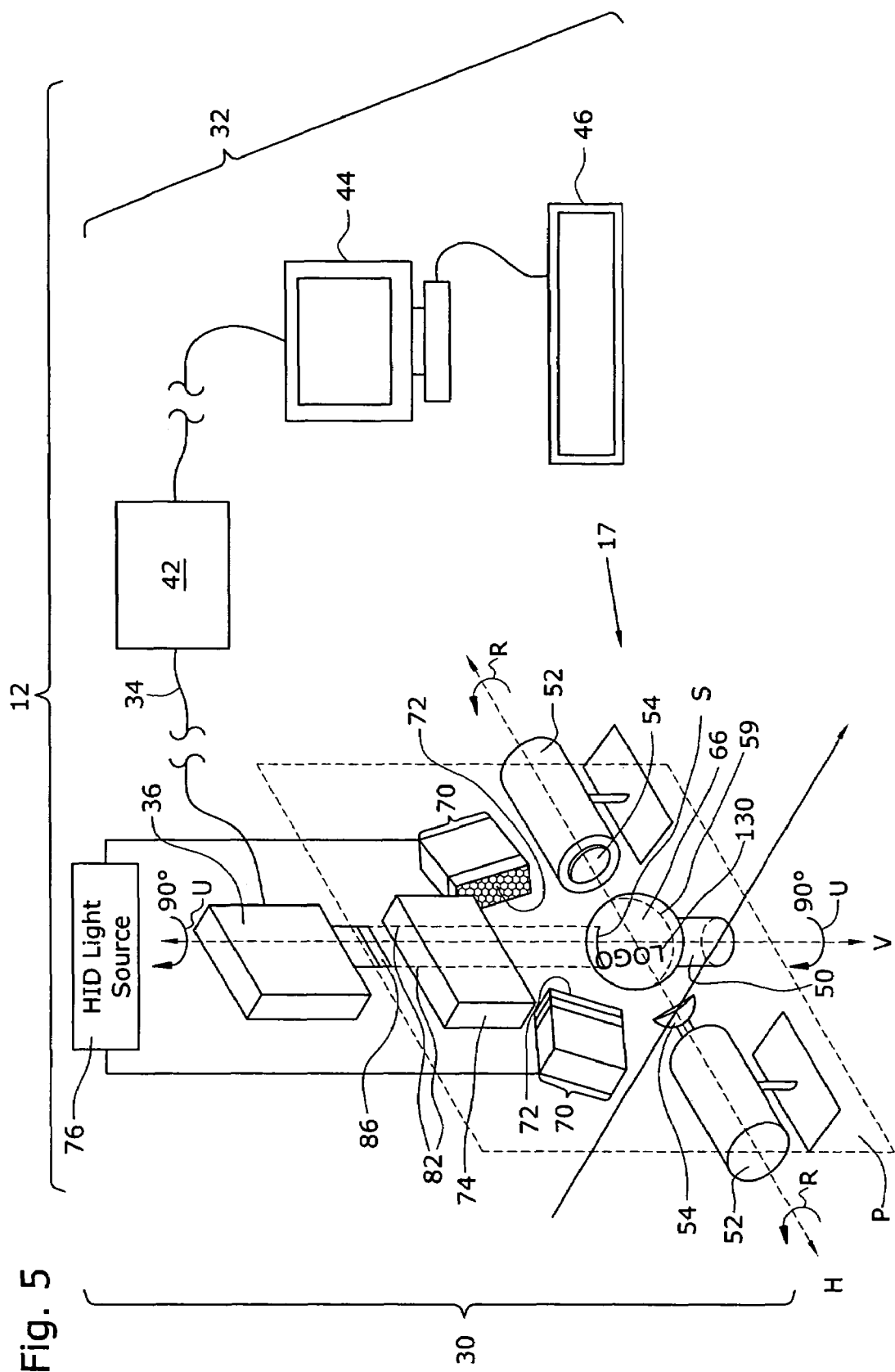
FIG. 5 is a perspective view of the golf ball as it is about to be rotated and scanned by an imaging system and a schematic illustration of an automated analyzer, according to the present invention.

Referring to FIG. 5, after golf ball 66 is marked with indicium 130, golf ball 66 is inspected to ensure compliance with a prescribed set of quality standards. The inspection of indicium 130 is automatically performed by camera 36, which is connected to high-speed vision engine 42. Vision engine 42 analyzes whether indicium 130 is acceptable by adjusting the detected image data of golf ball 66, so as to minimize curvature distortion, before comparing the adjusted image to a master image.

Automated inspection system 12 inspects golf ball 66 at inspection station 17 and comprises imaging system 30 and automated analyzer 32 linked together via an electronic link 34, which can be wireless. Detector 36 of imaging system 30 views and detects golf ball 66 and provides an inspection signal, i.e., data used to assemble a two-dimensional image of golf ball 66, into automated analyzer 32.

In one embodiment, detector 36 is a line scan camera suitable for analyzing golf balls. In one embodiment, camera 36 is an electronically shuttered, solid-state CCD (charged coupled device) SP-14-01k40 model line scan detector, obtainable from Dalsa, Inc. Waterloo, Ontario, Canada. Other detectors such as an area scan camera, can be used with the present invention.

Figure 10:
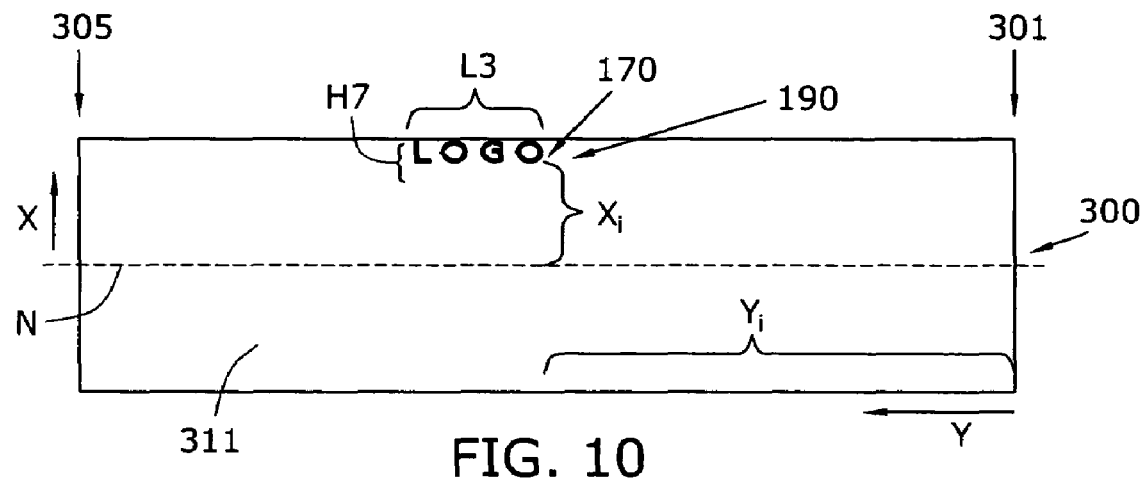
FIG. 10 is a plan view of a two-dimensional scanned image made by the imaging system in FIG. 5, that has curvature distortion, according to the present invention.

In the first step of acquiring an inspection image, golf ball 66 is scanned, repositioned, and scanned again to ensure that its entire surface is inspected. Stepper motors 52 engage golf ball 66 with suction cups 54 and rotate golf ball 66 at least one revolution about horizontal axis H in the direction indicated by direction arrows R. As golf ball 66 rotates, imaginary line 59 falls under scan line S, and line scan camera 36 begins to scan ball 66 along scan line S. Once golf ball 66 is scanned, suction cups 54 release golf ball 66, and holder cup 50 rotates golf ball 66 ninety degrees about vertical axis V, as indicated by direction arrows U. Stepper motors 52 engage golf ball 66 with suction cups 54 and rotate golf ball 66 a second time while line scan camera 36 scans golf ball 66 at scan line S. Both times golf ball 66 is rotated, line scan camera 36 collects pixel row image data, which when assembled is used to form two two-dimensional images of golf ball 66 that collectively depict the entire surface of golf ball 66. The first of these images is shown in FIG. 10 as image 300, which is described below.

As camera 36 scans golf ball 66, fiber optic light bundles 72 illuminate scan line S with diffuse, uniform, polarized light. In particular, fiber optic bundles 72 direct light from high intensity (HID) light source 76 towards golf ball 66. Suitable fibers are commercially available from Schott-Fotec, Inc., Auburn, N.Y. In one embodiment, HID light source 76 is a lamp that is DC stabilized to produce more uniform light. HID light source 76 can include, for example, a short arc, a metal halide, or a mercury vapor light. Metal halide light source is also available from Schott-Fotec, Inc. Light source 76 may alternately include quartz halogen, LED, fluorescent, incandescent, or any other suitable light source.

Scan line S curves along ball 66 and defines plane P. Therefore, to provide a more diffuse source of illumination onto scan line S, bundles 72 are arranged into lines 70 that direct light along plane P and onto scan line S. Lines 70 also direct light closely parallel to plane P. In one embodiment, lines 70 direct a minimum of off-axis light, i.e., from either side of scan line S, to avoid sideways illumination of scan line S. Rather, light is directed along plane P or closely parallel to plane P.

Figure 6:
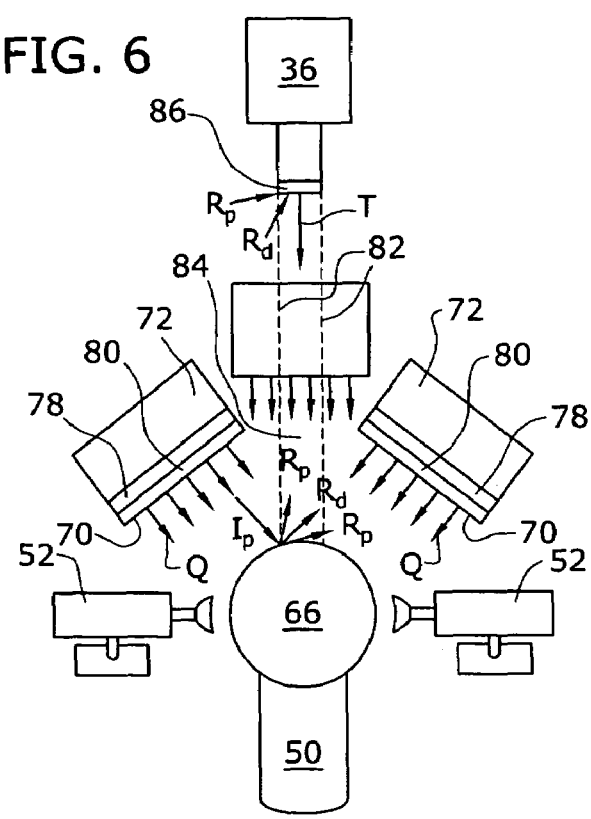
FIG. 6 is a front view of the imaging system of FIG. 5.

Referring to FIG. 6, lines 70 preferably direct light through lenses 78 and polarizers 80, which collectively emit substantially uniform, polarized light. Lenses 78 are mounted onto lines 70 to provide more uniform illumination along scan line S. Suitable lenses include the NT55-349 telecentric lens available from Edmunds Industrial Optics, Barrington, N.J. and the Computar Tec-55 lens available from Computer Optics Inc., Hudson, N.H. Polarizers 80, which are mounted onto lines 70, and analyzer 86 (camera 36's polarizer), which is mounted onto camera 36, are positioned so that their respective axes of polarization Q and T are about ninety degrees with respect to one another. Ninety degree angle is preferred since it minimizes the specular glare from the shiny surface of the balls. Other angles are also suitable if specular glare can be minimized or compensated by software. Configured as such, analyzer 86 blocks reflected light $R_p$ that has the same polarity as incident light $I_p$. As incident polarized light $I_p$ reflects off golf ball 66, it reflects as diffuse light $R_d$ and potentially glaring polarized light $R_p$. Camera 36 captures only the light that is not polarized by polarizers 80, including diffuse reflective light $R_d$. Because analyzer 86 will not allow any of the light polarized along axis Q to be detected by camera 36, glare is reduced. Suitable analyzer includes the R52-558 from Edmond Industrial Optics.

In another embodiment, diffuse on axis light source (DOAL) 74 can also illuminate scan line S. DOAL 74 uses a beam splitter (not shown), or half-silvered mirror (not shown), to direct light that is co-axial to camera 36's line of vision 82, into space 84 between bundles 72. Camera 36 can see through the beam splitter, and sufficient light is reflected into space 84 so that scan line S is more uniformly illuminated. A suitable DOAL is described in U.S. Pat. No. 5,604,550, which is incorporated herein by reference in its entirety. DOAL devices are also commercially available from Northeast Robotics, Weare, New Hampshire, and Industrial Vision Systems, Ltd., Oxon, Great Britain. Preferably, the fiber optic system is combined with the HID light source for higher light output. A suitable combination includes a fiber optic co-axial beamsplitter illuminator (CADI) from Illumination Technologies, Syracuse, N.Y., and a Schott-Fostec HID source discussed above.

Figure 7:
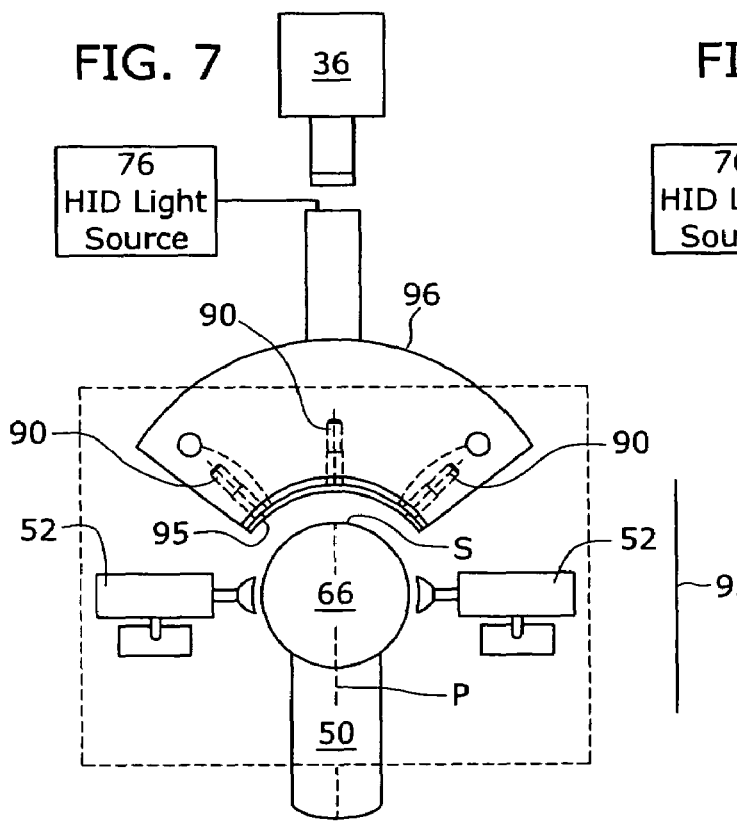
FIG. 7 is a front view of an alternate embodiment of an imaging system, according to the present invention.

Referring to FIG. 7, in an alternate embodiment, fiber optic bundles 91 are housed in curved arcs 96 that conform to the curvature of scan line S on golf ball 66. Curved light sources can diffuse light more efficiently on to a curved surface. Polarized lenses 95 are mounted onto arcs 96 at apertures 90 to prevent glare distortion in images taken by camera 36.

Figure 8:
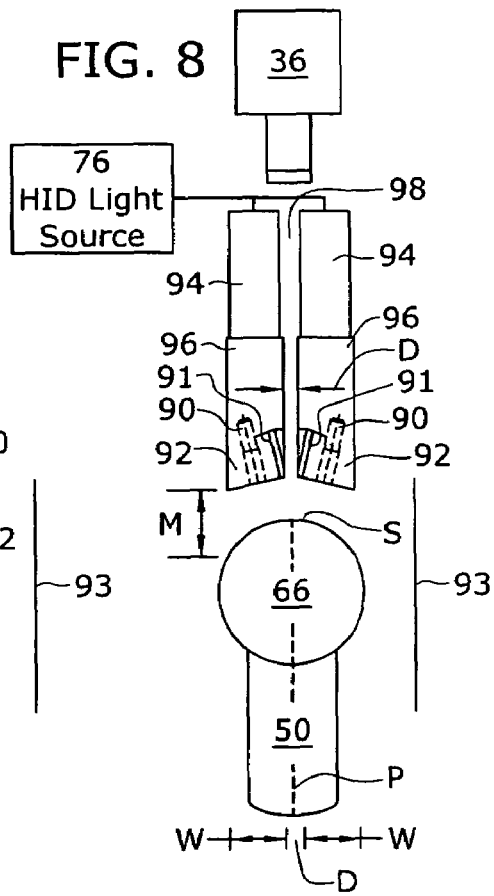
FIG. 8 is a side view of the imaging system in FIG. 7 showing a partial cross-section of the curved light source.

As shown in FIG. 8, camera 36 scans golf ball 66 along scan line S through gap 98, which is defined by light conduits 94. Arcs 96 provide a substantially uniform, solid arc of illumination to scan line S, which defines plane P. Space M between arcs 96 and scan line S on golf ball 66 is configured and dimensioned for golf ball geometry, as discussed below. As arcs 96 are moved away from golf ball 66, lighting intensity decreases and off-axis lighting increases in proportion to widths W of arcs 96 and gap distance D. To recapture lost light intensity, mirrors 93 can be placed parallel to plane P to reflect light back.

Bundles 91 direct light from light source 76 so that it travels along conduits 94 and parallel to plane P. The round bundle is fanned out to make a continuous line light source, similar to the way a straight line light is made. The bundles direct light so that it forms a section of a cone whose vertex angle is about 154 degrees (13 degrees from planar). The cone is symmetrical about the axis of rotation of the ball and intersects the surface of the ball at the scan line S.

Gap distance D between arcs 96 is minimized to diminish off-axis lighting. In one embodiment, gap distance D is between about 0.01 and 0.03 inches (about 0.254–0.735 mm). At respective ends 92 of arcs 96, bundles 91 are positioned at a predetermined distance away from scan line S and at a predetermined angle to scan line S. Referring to FIG. 8, this predetermined angle is the angle between horizontal and the surface of end 92, or the angle between vertical (or plane P) and the direction of the light emitting from bundles 91. Preferably, the end of bundles 91 where light exits can be positioned from about 0.630 mm to scan line S and at an angle of about 6 degrees to about 0.100 mm and at angle of about 33 degrees. More preferably, light exits from about 6.25 mm to line S and at about 13 degree angle with respect to plane P, so that light is focused onto scan line S.

Figure 9:
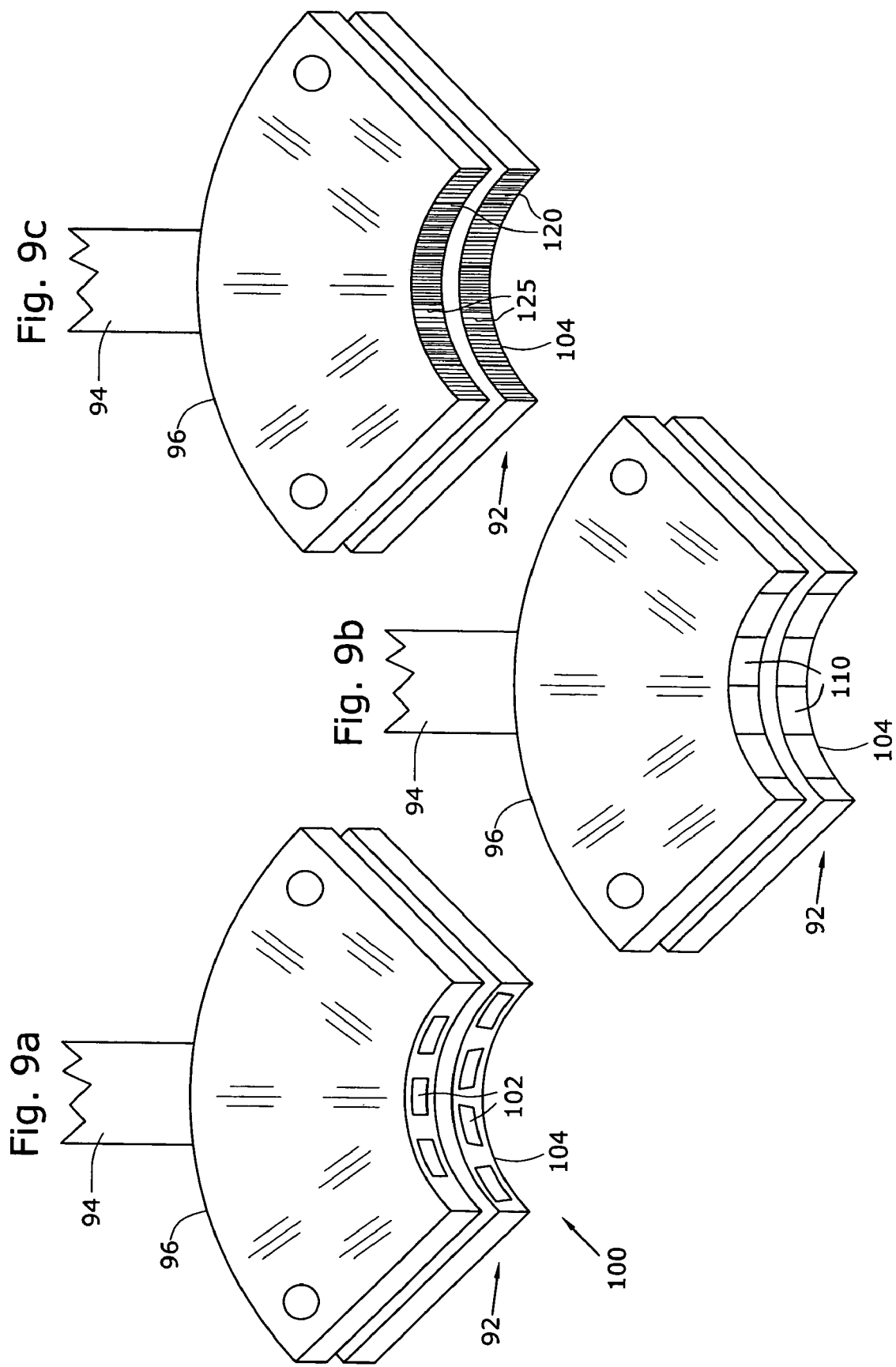
FIG. 9a is a cut-away bottom perspective view of the light conduits in FIGS. 7 and 8.
FIG. 9b is a cut-away bottom perspective view of an alternate embodiment of the light conduits.
FIG. 9c is a cut-away bottom perspective view of another alternate embodiment of the light conduits.

As shown in FIG. 9a, in one embodiment the uniformity of illumination along scan line S is enhanced by directing light through aperture array 100, which is connected to ends 92 of arcs 96. Apertures 102 have varying adjustable widths that can be opened and closed to increase the uniformity of lighting that emits from along curved line 104. As shown in FIG. 9b, in an alternate embodiment, array 110 of polarizing filters is similarly used to adjust the uniformity of light that emits from various positions along lines 104. As shown in FIG. 9c, in another alternate embodiment, fine comb-like structures 120 having teeth 125 of varying pitch are used to adjust the uniformity of light that emits from various positions along lines 104.

In one embodiment, a digital filter program automatically adjusts the uniformity of the light emitted from lines 104, as is described below as part of the following detected image data adjustment step.

After scanning, the data that makes up the detected image is adjusted to digitally filter non-uniform lighting and to minimize curvature distortion. One suitable analysis system for these and other analyses is described in the '998 patent, previously incorporated herein by reference in its entirety. Referring to FIG. 5, analyzer 32 receives the inspection signal of scanned golf ball 66 from camera 36 and adjusts the detected data. In one embodiment, analyzer 32 performs various analytical tasks, such as data processing, task scheduling, generation of rejection signals or further control signals, and/or alarms. Analyzer 32 can also record the detected and adjusted images of inspected golf ball 66 for future reference. Analyzer 32 may be placed near, and in one embodiment adjacent, to the operator to enable easy and quick access to both analyzer 32 (to view a defect) and inspection station 17 (to attend to and to correct the cause of a defect). Analyzer 32 includes a high-speed vision engine 42, which includes a computer processor, a monitor 44 and keyboard 46, among other components.

More specifically, vision engine 42 analyzes the detected image data that camera 36 transmits and adjusts the detected image data. It also compares the adjusted image with a master or reference image. In one embodiment, a variety of inspection routines may be performed by vision engine 42, such as further data analysis and adjustment of such data to digitally filter the detected brightness levels to achieve a uniform baseline adjusted brightness level in the adjusted images. This corrects non-uniform lighting conditions along scan line S, and is described in greater detail below. This method of compensating for uneven lighting is usable for image acquisition by both line scan and area scan cameras.

Referring to FIGS. 5 and 10, in one embodiment before the detected data is adjusted, it is assembled into a distorted image. Once detection data is sent from camera 36 to analyzer 32, analyzer 32 assembles the detected image data to form line scanned image 300 shown in FIG. 10. Image 300 is made up of multiple rows of pixel data. First pixel row 301 is the first row to be scanned (at scan line S), and last pixel row 305 is the last row to be scanned (at scan line S). Each image can be about 256 pixels to about 4096 pixels wide, and more preferably, each image is about 1024 pixels wide. Each pixel corresponds to a two-coordinate position on ball 66 as notated in FIG. 10 according to coordinate axes Y and X. Line N designates an equatorial line on ball 66 above which a point has a positive "X" value, and below which a point has a negative "X" value. Image 300 specifically depicts the first scan of golf ball 66. Thus, each scanned surface portion of ball 66, including indicium 130, is represented by corresponding pixel data.

Image 300 depicts indicium 130 as logo image portion 190, which contains curvature distortion. For example, length L3 is disproportionately longer and height H7 is shorter, as compared with the actual height and length of indicium 130. More particularly, the bottom right portion of the second "O" in "LOGO" (of indicium 130) is represented at pixel 170 as having a distorted, detected position ($Y_i$, $X_i$) in image 300. This data point serves as an exemplary data adjustment value in the two detected image adjustment embodiments described below. In an alternate embodiment, detected image data is adjusted without assembling a detected image. Whether image 300 is assembled does not retract from its usefulness in describing the digital filtering and curvature distortion adjustment of detected data. Furthermore, this curvature correction method can be applied to any digital image, regardless of how the image was obtained.

Figure 11:
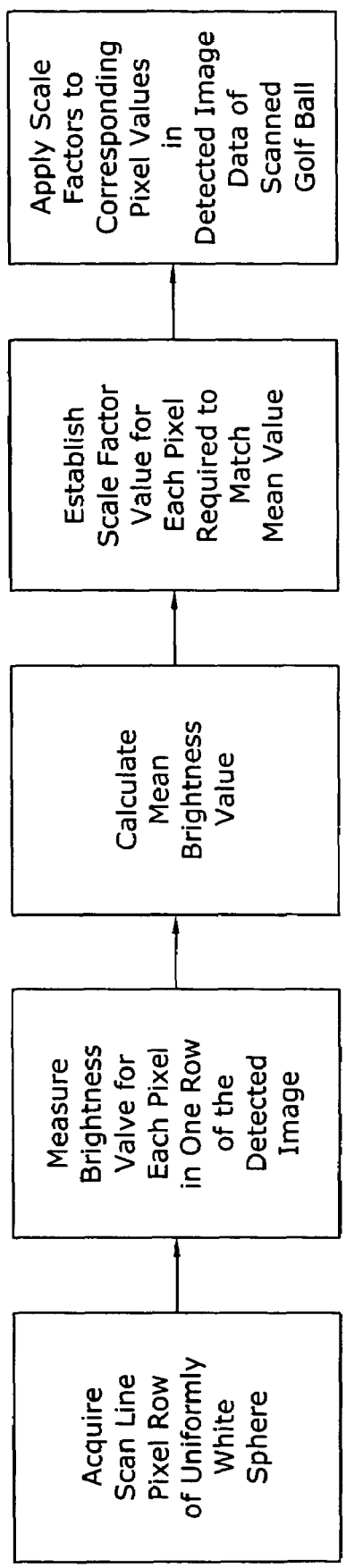
FIG. 11 is a schematic depiction of a method of digitally filtering brightness levels in inspected images, according to the present invention.

Referring to FIGS. 5 and 10, to the extent that scan line S was not uniformly illuminated as golf ball 66 was scanned, the brightness values of each pixel in pixel matrix 311 can be adjusted to create an image that displays pixel data as though it were gathered under uniform brightness conditions. In one embodiment, analyzer 32 runs a digital filter program to automatically adjust detected image data and thus account for non-uniform lighting during scanning of ball 66. Referring to FIG. 11, before inspecting golf ball 66, a uniformly white ball is placed at station 17 where scan line camera 36 scans an image including at least one scan line pixel row and preferably the entire surface of the ball. Relative brightness values for each pixel in a row of data are measured and stored. A mean brightness value is calculated from these values, or another reference value is selected. A scale factor for each pixel in the row is then calculated by taking the difference between each pixel's brightness value and the mean or reference value. The scale factor for each pixel is applied to corresponding pixel data for inspected images to adjust their brightness values. This adjustment can be represented by the formula V=M×(I/C), where M is the maximum gray value for a fixed pixel, I is the gray value for a particular pixel in the inspection image and C is the value for that same pixel obtained during calibration. The pixels' scale factors can be similarly applied to corresponding data for pixels having the same horizontal image position in subsequently scanned lines.

Figure 12:
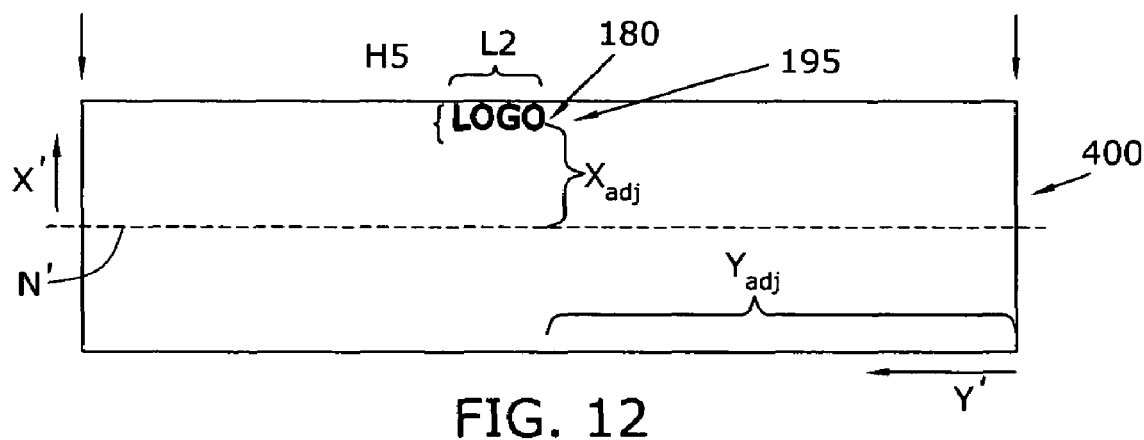
FIG. 12 is a plan view of a two-dimensional image made from the adjusted data of the image in FIG. 10, according to the present invention.

Detected image data from image 300 is then adjusted to minimize curvature distortion. In one embodiment, analyzer 32 locates logo image portion 190 using a matching algorithm or blob analysis and removes the distortion locally by transforming pixel values in image 300 to new pixel values in image 400 of FIG. 12. Referring to FIGS. 5 and 10, analyzer 32 for example adjusts the letter "O" data point represented at pixel 170 from its position at $Y_i$,$X_i$ in image 300, to pixel 180 at position $Y_{adj}$,$X_{adj}$ in FIG. 12, according to the following formula:

$$X_{adj}=R \cdot \text{arcsine}(X_i/R)$$

where $X_i$ is the observed distance along coordinate axis X of distorted image 300 in FIG. 10, R is the radius of ball 66, and $X_{adj}$ is the new, adjusted distance along coordinate axis X' of adjusted image 400 in FIG. 12. R and X should have the same length unit. The operation of arcsine ($\sin^{-1}$) is taken in radian units. All pixel data in the X direction in image 300 is adjusted according to this formula to produce new pixel data that is displayed in image 400.

The pixel data in the Y direction can be corrected locally by finding the center of the indicia to be inspected (or any other reference point) and correcting Y positions relative to that reference point and in accordance to the following formula:

$$Y_{adj}=C-((C-Y_i)/\cos \theta),$$

where $\theta$ is the angular location above or below the equator of the pixels being adjusted. This formula is suitable for correction of relatively smaller indicia. Larger indicia near the edge of the line scan image will distort from curvature as the $Y_i$ location gets further from the reference point C.

In addition, a second line scan image can be obtained after rotating the ball about an axis perpendicular to the axis used for scanning the ball. This second image will contain information not included in the first image. As this information is mapped onto the sphere, as described above, a composite image of the ball is formed. In places where indicia runs off the end of the image or where pieces of the composite overlap, part or all of the indicia may be used in a pattern matching algorithm to align the pieces of the composite so that the seams don't interfere with inspection. This method can be applied with multiple area scan images as well as with multiple line scan images.

Another preferred method is to convert the line scan pixel data into polar coordinates $\theta$ and $\phi$. This doesn't require a local transformation. The whole line scan can be mapped onto a sphere before the indicia is located and inspected.

Figure 13:
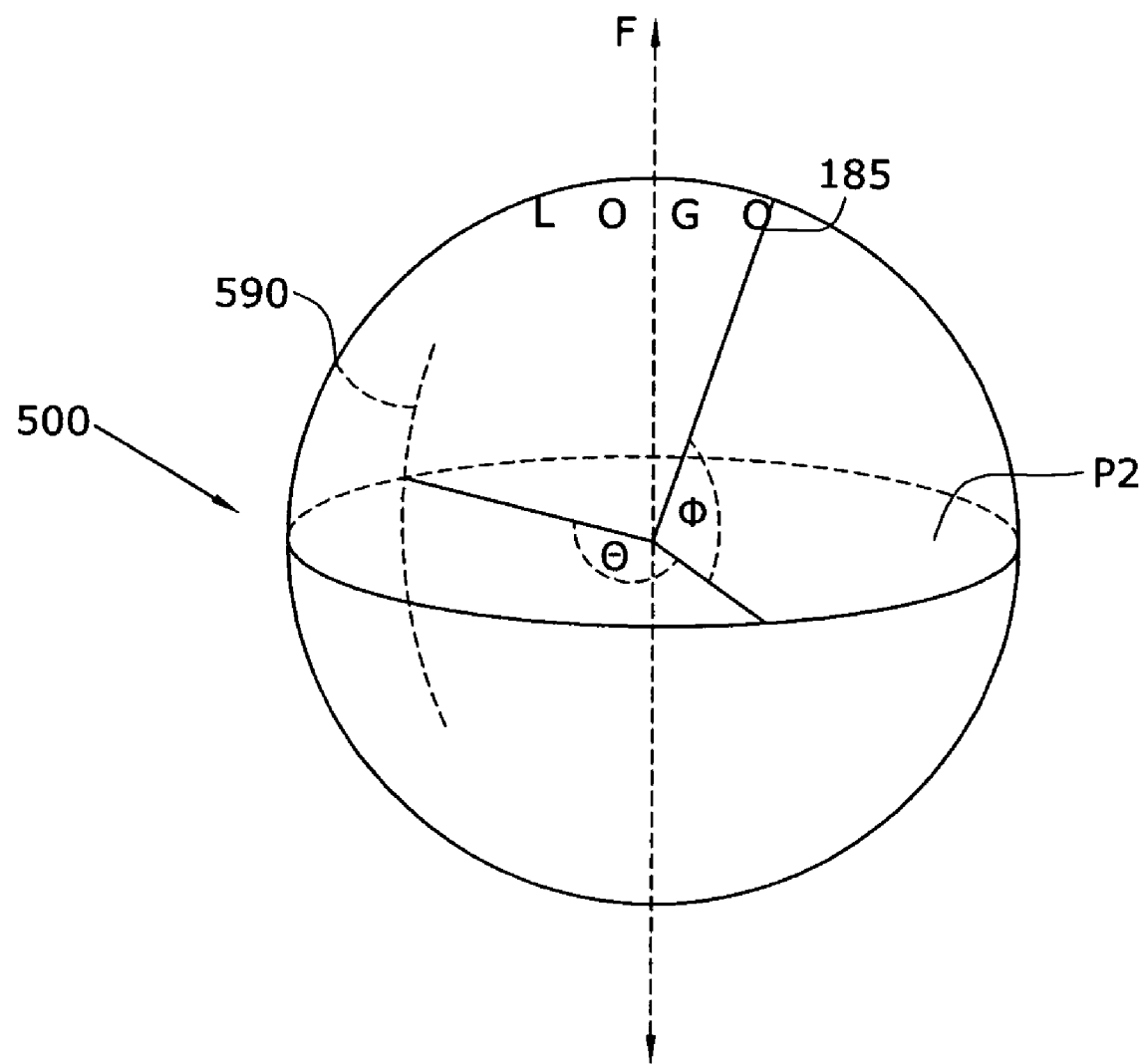
FIG. 13 illustrates a three-dimensional digital spherical model that displays data adjusted from the data of the image in FIG. 10, according to the present invention.

As shown in FIGS. 5, 10 and 13, in an alternate embodiment analyzer 32 refits or remaps data that form detected image 300 to new data points on three-dimensional digital, spherical model 500. Analyzer 32 first locates logo image portion 190 using a matching algorithm or blob analysis and removes the distortion locally by transforming pixel values in image 300 to new pixel values in spherical model 500 of FIG. 13. Data points that form image 300 are converted according to the following formulas:

$$\theta=(2\pi)(Y/R)$$

where $\theta$ is the angular position about spherical axis of rotation F (corresponding to golf ball 66's rotational axis U) beginning at imaginary line 590 (corresponding to line 59 on ball 66 where camera 36 begins scanning data), $Y_i$ is the initial distance along the Y axis on distorted image portion 190, and R is the radius of the golf ball. Additionally, $$\Phi=\text{arcsine}(X_i/R)$$

where $\Phi$ is the angular position above or below equatorial plane P2 that dissects spherical model 500 perpendicular to axis F, and $X_i$ is the initial distance along axis X on distorted image 300. For example, the letter "O" data point represented at pixel 170 in FIG. 10 is adjusted from its position at $Y_i, X_i$ in image 300, to point 185 on model 500 in FIG. 13.

Referring to FIGS. 5 and 12, analyzer 32 then performs the third step of comparing adjusted image 400 with a master image to determine if ball 66 complies with acceptable indicium standards. In this step, indicium 130 is ultimately inspected using an algorithm that analyses the adjusted image data of indicium 130. Suitable algorithms include, but are not limited to, pattern matching, pattern inspecting, image inspecting, image comparing or image subtracting algorithms such as Patinspect or Flexinspect tools obtainable from Cognex Corp. of Natick, Mass.

Alternatively, since each pixel has a numerical brightness value on a gray scale or each pixel can be converted into a black or white pixel, the brightness values of all the pixels can be summed up to obtain a total brightness value. This total value can be compared to a master value by the inspection system. If the difference between them is within an acceptable range, then the scanned image is acceptable. Preferably, this method is used after non-uniform brightness and curvature distortion have been corrected.

After the curvature distortion has been removed by replacing the scanned data with the adjusted data, image portion 195 is compared with a digitally generated image portion of the word "LOGO," comprising a suitable font having a suitable size and shape. In one embodiment, suitable bit map images having suitable sizes and shapes can be used to create the digitally generated image.

Referring to FIGS. 5 and 13, in an alternate embodiment analyzer 32 compares data adjusted to fit spherical model 500 with a master three-dimensional spherical data image comprising a suitable font having a suitable size and shape. In one embodiment, suitable bit map images having suitable sizes and shapes can be used to create the digitally generated image.

In accordance to another aspect of the present invention, another image correction technique can be used when the center of the ball does not coincide with the location where image system focuses. In this event, the angle θ is replaced by (X+E)/R, where E is the error in the X direction and is measured from the true center C of ball 66 to the center of the image (or location where the camera focuses or where the software expects the center of the ball to be). The sketch below illustrates the distance E.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments that would come within the spirit and scope of the present invention.

We claim:

1. A method of inspecting a curved object, comprising:
   acquiring an inspection image of a curved object using a detector;
   adjusting the inspection image to minimize curvature distortion in an adjusted image; and
   comparing the adjusted image with a predetermined master image;
   further comprising the step of adjusting the brightness values of the image to account for non-uniform illumination, wherein the step of adjusting the brightness comprises the steps of acquiring a scanned image of a uniformly shaded object; measuring brightness values for each pixel in said scanned image; calculating a reference brightness value; establishing scale factors for each pixel in said scanned image based on the reference brightness value; and adjusting corresponding pixel brightness values in the inspection image by applying the scale factors for correcting of curvature distortion.

2. The method of claim 1 wherein the object is a golf ball.

3. The method of claim 2 wherein the detector is a line scan camera that scans the object at a scan line that defines a plane.

4. The method of claim 3 wherein the object is illuminated with light directed along a plane or a conical section while acquiring the inspection data.

5. The method of claim 4 wherein the object is illuminated with light directed parallel to the plane while acquiring the inspection data.

6. The method of claim 4 wherein the light is arranged in a line.

7. The method of claim 6 wherein the line comprises a linear array of fiber optic bundles that direct the light from at least one light source.

8. The method of claim 7 wherein the bundles define a gap through which the scan line is directed.

9. The method according to claim 7 wherein the at least one light source comprises a high intensity discharge light.

10. The method of claim 6 wherein the line directs the light through at least one lens to provide more uniform illumination along the scan line.

11. The method of claim 6 wherein the line conforms to a curved surface of the object.

12. The method of claim 4 wherein the light is polarized according to an illuminating axis of polarization, and a lens for the camera is polarized according to a detecting axis of polarization, wherein the illuminating and detecting axes are configured with respect to one another to reduce glare.

13. The method of claim 12 wherein the illuminating and detecting axes are positioned at about 90-degree angle to one another.

14. The method of claim 4 wherein a diffuse, on-axis light source provides supplemental light.

15. The method of claim 4 wherein a mirror is used to reflect light towards the scan line.

16. The method of claim 4 further comprising the step of adjusting the light to account for non-uniform object illumination at the scan line.

17. The method of claim 16 wherein the light is directed through an aperture having varying widths along the line.

18. The method of claim 16 wherein the light is directed through a comb-like structure having members with varying pitch.

19. The method of claim 16 wherein the light is directed through polarizers having varying angles of polarization with respect to each other.

20. The method of claim 1 wherein the inspection image is a two-dimensional image.

21. The method of claim 1 wherein the adjusted image is a three-dimensional image.

22. The method of claim 1 wherein the detector is an area scan camera.

23. A method for inspecting a curved object comprising the steps of
   acquiring an image of a white calibration object as a predetermined master image;
   acquiring an inspection image of a curved object using a detector; and adjusting the inspection image to adjust the brightness to account for non-uniform illumination comprising the steps of measuring brightness values for each pixel in the master image; calculating a reference brightness value; establishing scale factors for each pixel in the master image based on the reference brightness value; and adjusting corresponding pixel brightness values in the inspection image by applying the scale factors for correcting of curvature distortion.

24. The method of claim 23, wherein of adjusting the inspection image's further comprises the steps of applying the formula V=M×(I/C), where M is the maximum gray value for a fixed pixel, I is the gray value for a particular pixel in the inspection image and C is the value for that same pixel obtained during calibration.

25. The method of claim 24, wherein M is 255.

26. A method of inspecting a curved object, comprising:
acquiring an inspection image of a curved object using a detector;
adjusting the inspection image to minimize curvature distortion in a adjusted image; and
comparing the adjusted image with a predetermined master image for correcting of curvature distortion;
wherein the step of adjusting the inspection image to minimize curvature distortion comprises the steps of:
adjusting at least one pixel in the inspection image in one direction using the formula:

$$X_{adj} = R \cdot \text{arcsine}(X_i/R); \text{ and}$$

adjusting said pixel in the other direction using the formula: $Y_{adj} = C - ((C - Y_i)/\cos \theta)$
where R is the radius of the curved object, (Xi, Yi) are the coordinates of said pixel, C is a reference point on the inspection image, $\theta$ is the angular location above or below the equator of the curved object, and $(X_{adj}, Y_{adj})$ are the coordinates of the adjusted pixel.

27. The method of claim 26 wherein all the pixels in the inspection image are adjusted.

28. The method of claim 26 wherein the curved object is a golf ball.

29. The method of claim 28 wherein C is a reference point of a logo on the golf ball.

30. The method of claim 29 wherein C is the center of the logo.

* * * * *